US00PP35866P2

(12) United States Plant Patent
Contreras

(10) Patent No.: US PP35,866 P2
(45) Date of Patent: Jun. 11, 2024

(54) ***HIBISCUS* PLANT NAMED 'ORSTHIB5X1'**

(50) Latin Name: *Hibiscus syriacus*
Varietal Denomination: ORSTHIB5X1

(71) Applicant: Oregon State University, Corvallis, OR (US)

(72) Inventor: Ryan N. Contreras, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 44 days.

(21) Appl. No.: 18/113,485

(22) Filed: Feb. 23, 2023

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257
CPC . A01H 5/02; A01H 5/00; A01H 6/608; A01H 6/60
See application file for complete search history.

(56) References Cited

U.S. PATENT DOCUMENTS

PP7,835 P * 3/1992 Moser ..... Plt./257
PP28,839 P3 * 1/2018 van Huylenbroeck ..... Plt./257

OTHER PUBLICATIONS

Hidden Valley *Hibiscus* Exotic *Hibiscus* 'Flamingo', retrieved on Jun. 8, 2023 at http://www.hiddenvalleynaturearts.com/info/flamingo.htm, 3 pp. (Year: 2023).*

International Code of Nomenclature for Cultivated Plants Ninth Edition 2016, ISHS, edited by Brickell et. al., two introductory pages, pp. 30-31. (Year: 2016).*

* cited by examiner

*Primary Examiner* — June Hwu
(74) *Attorney, Agent, or Firm* — Klarquist Sparkman, LLP

(57) ABSTRACT

A new and distinct *Hibiscus* plant cultivar named 'ORSTHIB5X1' is disclosed, characterized by its growth habit and form, deep green foliage that is resistant to chlorosis, seedlessness, and pentaploid chromosome complement.

2 Drawing Sheets

Latin name of the genus and species of the plant claimed: *Hibiscus syriacus.*

Variety denomination: 'ORSTHIB5X1'.

BACKGROUND

The present application relates to a new and distinct variety of *Hibiscus* named 'ORSTHIB5X1', which resulted from planned breeding in Corvallis, OR. 'ORSTHIB5X1' is a selection from a crossing between a tetraploid (4×) form of 'Aphrodite' (unpatented; 2C DNA content=4.66 pg) as the seed parent with hexaploid (6×) 'Pink Giant' (unpatented; 2C DNA content=6.97 pg) as the pollen parent. 'ORSTHIB5X1' was selected in 2013 and evaluated using flow cytometry, which confirmed it to be a pentaploid (5×) with 2C DNA content=5.4 pg. Its ploidy alone is distinct among available *Hibiscus syriacus* cultivars.

The plant was first propagated in 2015 in Corvallis, OR. In subsequent years, it was confirmed to maintain its ploidy, consistently dark green foliage, vigorous and compact growth form, and seedlessness.

SUMMARY

Plants of the new *Hibiscus* have not been observed under all possible combinations of environmental conditions and cultural practices. However, the following traits have been consistently observed and are a unique combination of characteristics for 'ORSTHIB5X1':

1. Upright to spreading growth form with erect branching
2. Deep green foliage that is less susceptible to chlorosis than other cultivars 3. Moderately vigorous, with compact growth form
4. Pentaploid chromosome complement that renders the plant seedless
5. Distinct and intermediate genome size (between its parents)
6. More compact than either parent Table 1 provides a comparison of 'ORSTHIB5X1' to its female parent, 'Aphrodite' to further illustrate its unique features.

Table 1. Comparison of 'ORSTHIB5X1' to its female parent, 'Aphrodite'. Color measurements collected in the CIEL*a*b* color space (L*a*b*) performed using a Nix Pro colorimeter. L* represents lightness, (0=black and 100=white), a* represents red/green color composition (−100=green and 100=red), and b* represents yellow/blue color composition (−100=blue and 100=yellow). These values were converted to R.H.S. color chips using a macro in Microsoft® Excel®.

TABLE 1

Comparison of 'ORSTHIB5X1' to its female parent, 'Aphrodite'.

| | 'ORSTHIB5X1' | | | |
|---|---|---|---|---|
| Color | L | a | b | RHS |
| Adaxial leaf color | 33.1 | −7.6 | 12.1 | 137A |
| Abaxial leaf color | 42.6 | −12.4 | 18.7 | 137B |
| Upper petal body | 55.8 | 35.2 | −8.5 | 186B |

TABLE 1-continued

| Comparison of 'ORSTHIB5X1' to its female parent, 'Aphrodite'. | | | | |
|---|---|---|---|---|
| Lower petal body | 58.9 | 29.4 | −1.1 | 186C |
| Eyespot | 28.4 | 36.2 | 11.5 | 59B |
| Calyx outer | 52.5 | −14.5 | 25.8 | 137D |
| Calyx inner | 49.5 | −13.1 | 27.4 | 146B |

| | 'Aphrodite' | | | |
|---|---|---|---|---|
| Color | L | a | b | RHS |
| Adaxial leaf color | 36.9 | −13.7 | 19.7 | 138A |
| Abaxial leaf color | 45.6 | −14.5 | 25.3 | 146A |
| Upper petal body | 61 | 31.2 | −8.1 | 70C |
| Lower petal body | 69 | 24.1 | −2.4 | 186D |
| Eyespot | 34.2 | 36 | 6 | 187C |
| Calyx outer | 48.1 | −12.8 | 23.1 | 138A |
| Calyx inner | 56.3 | −14.8 | 29.9 | 143A |

Color measurements collected in the CIEL*a*b* color space (L* a* b*) performed using a Nix Pro colorimeter. L* represents lightness, (0 = black and 100 = white), a* represents red/green color composition (−100 = green and 100 = red), and b* represents yellow/blue color composition (−100 = blue and 100 = yellow). These values were converted to RHS color chips using a macro in Microsoft ® Excel ®.

Size

| | | |
|---|---|---|
| Leaf length (with petiole) | 9.6 cm | 7.3 cm |
| Leaf blade length | 6.1 cm | 6.3 cm |
| Petiole length | 3.5 cm | 1.0 cm |
| Leaf width | 4.3 cm | 4.2 cm |
| Flower diameter | 7.8 cm | 8.4 cm |
| Peduncle length | 0.95 cm | 1.3 cm |
| Sepal length | 1.8 cm | 1.9 cm |
| Epicalyx length | 0.93 cm | 1.6 cm |

In addition, 'ORSTHIB5X1' is seedless and produces little or no pollen, whereas 'Aphrodite' produces a prolific amount of pollen, and a high number of capsules containing 17 seeds per capsule. Flowers of 'ORSTHIB5X1' are also darker and generally smaller than 'Aphrodite'.

'Pink Giant', the hexaploidy male parent of 'ORSTHIB5X1', produces 0.4 seeds per pollination as a female in test crosses and 1.6 seeds per pollination as a male. Fertility was lower in 'Pink Giant' than standard (single flower) tetraploids, but higher than 'ORSTHIB5X1'.

Asexual reproduction of this new variety by vegetative cuttings shows that the foregoing characteristics come true to form, are firmly fixed, and are established and transmitted through succeeding propagations.

Certain characteristics of this variety may change with changing environmental conditions (such as photoperiod, temperature, moisture, soil conditions, nutrient availability, or other factors). Thus, the phenotype may vary somewhat with variations in environmental conditions without any variance in genotype, including ploidy level.

Figure 1:
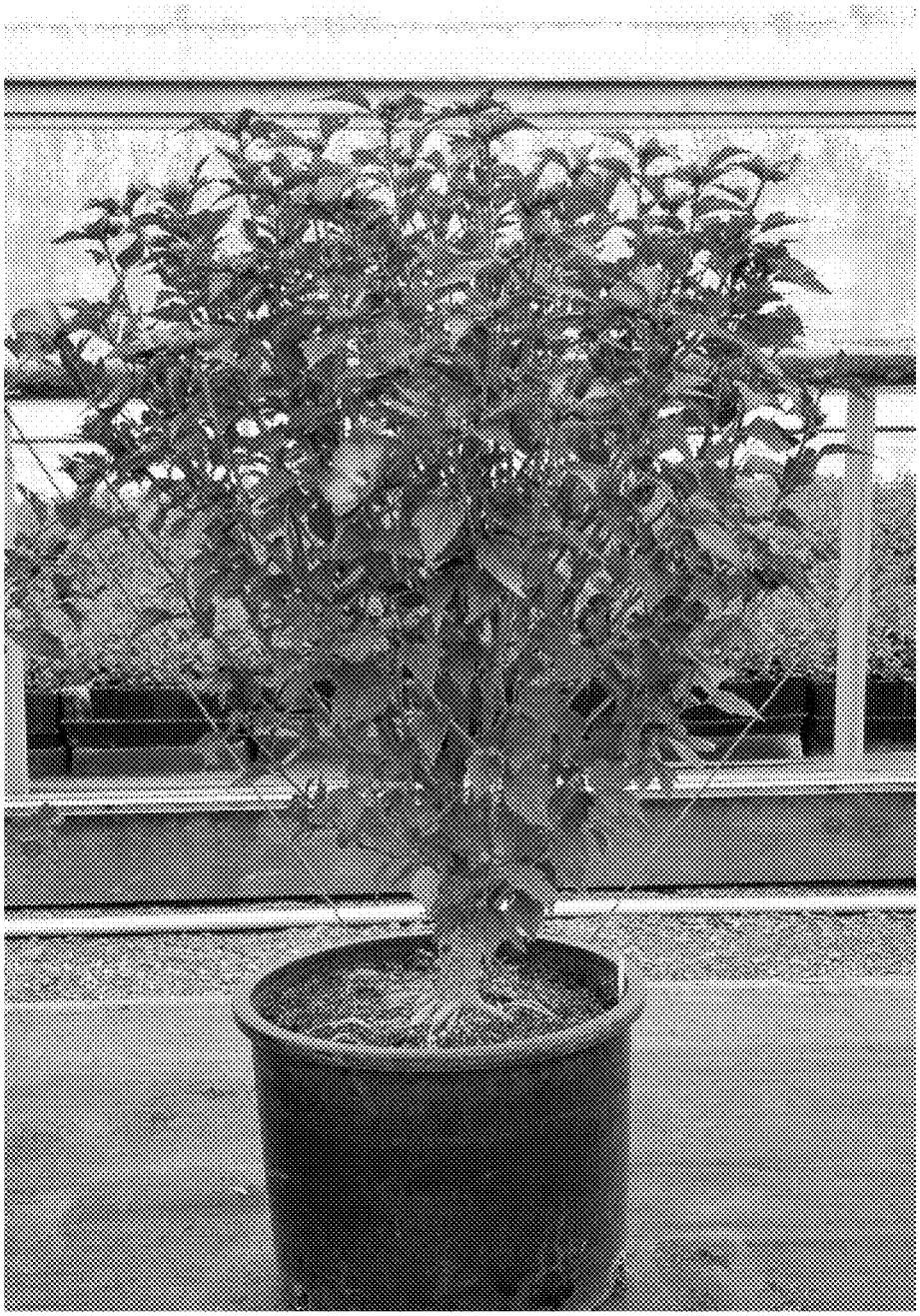
FIG. 1 is a photograph showing is a side perspective view of a typical container-grown plant of 'ORSTHIB5X1' grown in an outdoor nursery.
Figure 2:
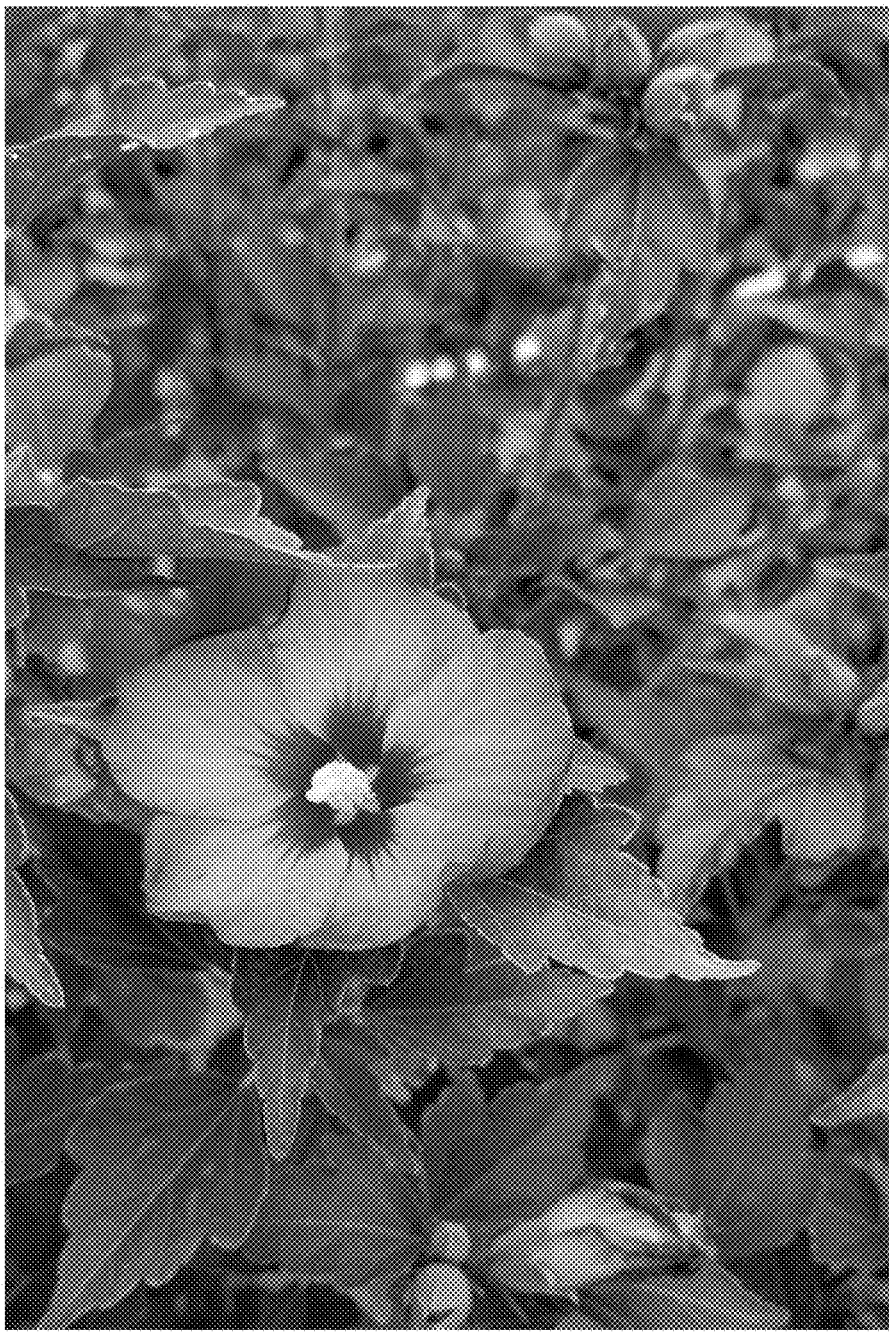
FIG. 2 is a photograph showing a typical flower of 'ORSTHIB5X1'.

The color photograph shows typical specimens of the new variety and depict the color as nearly true as is reasonably possible to make the same in a color illustration of this character. It should be noted that colors may vary, for example due to lighting conditions at the time the photograph is taken. Therefore, color characteristics of this new variety should be determined with reference to the observations described herein, rather than from the photograph alone.

DETAILED DESCRIPTION

The following is a detailed description while observing mature plants of the new following the rooting of stem cuttings. Such plants ranged between two and five years of age and were found to have consistent morphology, apart from size (younger plants are smaller). Plants were observed growing outdoors in full sun in Corvallis, Oregon, USA.

BOTANICAL

The following detailed description of the 'ORSTHIB5X1' variety is based on observations of mature plants that were asexually reproduced by rooting stem cuttings in Corvallis, OR. The observed progeny were two to five years of age and found to have consistent morphology, apart from size (younger plants are smaller). Plants were observed growing outdoors in full sun in a cultivated area in Corvallis, Oregon, USA, in Summer 2022.

The chart used in the identification of colors described herein is The R.H.S. Colour Chart (fifth edition) of The Royal Horticultural Society, London, 2007, except where general color terms of ordinary significance are used. The color values were determined in September 2022 under natural light conditions in Corvallis, Oregon, USA.

Scientific name: *Hibiscus syriacus*.

Parentage:

*Seed parent.*—*Hibiscus syriacus* 'Aphrodite' (tetraploid accession).

*Pollen parent.*—*Hibiscus syriacus* 'Pink Giant' (hexaploid).

Plant:

*Vigor.*—Moderate.

*Growth habit.*—Compact perennial shrub, upright to outwardly spreading with erect branching.

*Branching habit.*—Freely branching, creating a dense shrub.

*Lateral branch.*—224.24 mm long and 3.7 mm in diameter, internodes 24-28 mm, texture is slightly pubescent, color is RHS 199B with RHS 166A undertone.

*Plant height.*—About 85 cm.

*Plant diameter.*—About 60 cm.

Leaves:

*Size.*—Length: 9.6 cm (including the petiole). Width: 4.3 cm.

*Petiole.*—3.5 cm long and 1.1 cm in diameter, slightly pubescent surface texture, color is RHS 137B.

*Shape.*—Lobed, roughly rhomboidal.

*Apex.*—Acute.

*Base.*—Cuneate.

*Margin.*—Lobed.

*Lobes.*—Three prominent lobes with medium lobing and margin incision few to medium.

*Arrangement.*—Alternate, simple.

*Size of blade.*—6.1 cm.

*Leaf color.*—Adaxial surface: RHS 137A. Abaxial surface: RHS 137B.

*Leaf texture.*—Upper and lower surfaces are coriaceous with distinct venation.

*Venation pattern.*—Palmate.

Flowers:

*Bud*.—Ovoid, 13.2 mm long and 7.7 mm diameter at widest point, RHS 138B in color.

*Appearance and arrangement*.—Single flowers of moderate size, located mostly terminal; flowers face upright and outward.

*Flower diameter*.—7.8 cm.

*Flower length* (*height*).—4 cm.

*Flower shape*.—Broad campanulate.

*Petals*.—Petal Arrangement and Quantity: Single whorl of five or six petals strongly overlapping, petals mostly imbricate, no incision and weak undulation. Length: 4.3 cm. Width: 3.7 cm. Shape: Broadly obovate. Apex: Obtuse. Base: Attenuate. Color: Upper Surface: RHS 186B. Lower Surface: RHS 186C. Eyespot: Medium in size, color of eyespot and extensions are RHS 59B, extensions of eyespot are short. Margin: Entire. Lobation: Variable.

*Stamen number:* 55 per flower.

*Stamen*.—Filament is 0.8 mm long, anthers 1.2 mm long, anther color is RHS 11C.

*Stigma*.—1.1 mm long, RHS 155A in color.

*Style*.—22.4 mm.

*Pollen abundance*.—None observed.

*Peduncle length*.—0.95 cm.

*Peduncle texture*.—Slightly pubescent, strength is moderately pliable.

*Peduncle color*.—RHS 137B.

*Sepals*.—Length: 1.8 cm. Lobe length: 1.1 cm. Width (at base): 0.94 cm. Shape: Deltoid. Apex: Acute. Margin: Entire. Color: Upper Surface: RHS 137D. Lower Surface: RHS 146B.

*Calyx*.—Arrangement and Quantity: Single whorl of five sepals, each 1.8 cm long, fused into calyx with free lobes of 1.1 cm. Color: Outer RHS 137D; inner 146B. Sepal Length: 1.8 cm. Sepal Width: 0.9 cm.

*Epicalyx*.—Arrangement and quantity: Single whorl of seven or eight sepals. Sepal length: 0.93 cm. Sepal width: 0.15 cm. Sepal shape: Near acicular.

*Date of bloom*.—Mid- to late-summer in Corvallis, OR; earlier flowering that continues into the fall is expected in regions with warmer summers.

*Lastingness of individual blooms*.—Two to three days; self-cleaning.

*Fragrance*.—None.

*Number of seeds*.—None; seedless.

Hardiness: Hardiness has not been evaluated outside of Corvallis OR, which is USDA Zone 8b.

Disease/pest resistance: Not shown to be resistant to pathogens and pests common to *Hibiscus* plants.

I claim:

1. A new and distinct variety of *Hibiscus* plant named 'ORSTHIB5X1', substantially as illustrated and described herein.

* * * * *